(12) United States Patent
Czarnik

(10) Patent No.: US 7,915,309 B2
(45) Date of Patent: Mar. 29, 2011

(54) DEUTERIUM-ENRICHED OSELTAMIVIR

(75) Inventor: Anthony W. Czarnik, Reno, NV (US)

(73) Assignee: Protia, LLC, Reno, NV (US)

( * ) Notice: Subject to any disclaimer, the term of this patent is extended or adjusted under 35 U.S.C. 154(b) by 0 days.

(21) Appl. No.: 11/765,668

(22) Filed: Jun. 20, 2007

(65) Prior Publication Data

US 2008/0319064 A1 Dec. 25, 2008

(51) Int. Cl.
*A61K 31/215* (2006.01)
*C07C 229/46* (2006.01)

(52) U.S. Cl. ........................ 514/529; 560/125

(58) Field of Classification Search ........................ None
See application file for complete search history.

(56) References Cited

U.S. PATENT DOCUMENTS

| | | | |
|---|---|---|---|
| 5,763,483 A | 6/1998 | Bischofberger et al. | |
| 6,221,335 B1 * | 4/2001 | Foster | 424/1.81 |
| 6,440,710 B1 * | 8/2002 | Keinan et al. | 435/148 |
| 6,603,008 B1 * | 8/2003 | Ando et al. | 546/269.7 |
| 7,517,990 B2 * | 4/2009 | Ito et al. | 546/184 |
| 2007/0082929 A1 * | 4/2007 | Gant et al. | 514/338 |
| 2007/0197695 A1 * | 8/2007 | Potyen et al. | 524/110 |

FOREIGN PATENT DOCUMENTS

WO 95/26325 A2 10/1995

OTHER PUBLICATIONS

Oliyai et al, Pharmaceutical Research, Biexponential Decomposition of a Neuraminidase Inhibitor Prodrug (GS-4104) in Aqueous Solution, 1998, 15(8), pp. 1300-1304.*
Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982).*
Wolen, Journal of Clinical Pharmacology 1986; 26: 419-424.*
Browne, Journal of Clinical Pharmacology 1998; 38: 213-220.*
Baillie, Pharmacology Rev. 1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol. 1999; 39: 817-825.*
Honma et al., Drug Metab Dispos 15 (4): 551 (1987).*
Siegel, Marshall M.; Applied Spectroscopy (1989), 43(7), 1215-22.*
Plachy et al, Journal of Labelled Compounds and Radiopharmaceuticals, Synthesis of Di-t-alkyl Nitroxides Enriched in 2H and 12C, 1990, 28(1), pp. 99-110.*
Aldrich, Aldrich Handbook of Fine Chemicals and Laboratory Equipment, 2002, p. 21.*
Kushner, D.J.; Pharmacological Uses and Perspectives of Heavy Water and Deuterated Compounds; Canadian Journal of Physiology and Pharmacology 1999, 77(2), 79-88.
Oliyai et al.: Pharmaceutical Research, Biexponential Decomposition of Neuraminidase Inhibitor Prodrug (GS-4104) In Aqueous Solution; 1998 15(8) pp. 1300-1304.
Sweeny, D.J., et al., Metabolism of the Influenza Neuraminidase Inhibitor Prodrug Oseltamivir in the Rat, Drug Metabolism and Disposition 2000, 28)7), 737-41.
PCT/US09/67425 International Search Report and Written Opinion (corresponding PCT application) mailed Sep. 29, 2008.

* cited by examiner

*Primary Examiner* — Paul A Zucker

(74) *Attorney, Agent, or Firm* — Vance Intellectual Property, PC

(57) ABSTRACT

The present application describes deuterium-enriched oseltamivir, pharmaceutically acceptable salt forms thereof, and methods of treating using the same.

3 Claims, No Drawings

DEUTERIUM-ENRICHED OSELTAMIVIR

FIELD OF THE INVENTION

This invention relates generally to deuterium-enriched oseltamivir, pharmaceutical compositions containing the same, and methods of using the same.

BACKGROUND OF THE INVENTION

Oseltamivir, shown below, is a well known neuraminidase inhibitor.

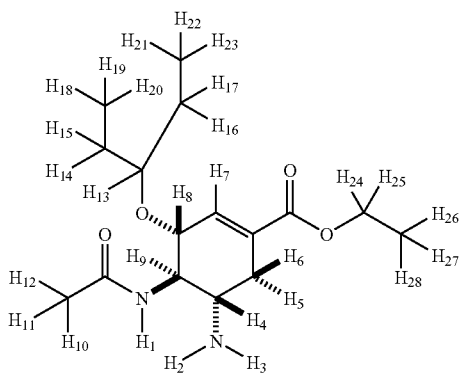

Since oseltamivir is a known and useful pharmaceutical, it is desirable to discover novel derivatives thereof. Oseltamivir is described in U.S. Pat. No. 5,763,483; the contents of which are incorporated herein by reference.

SUMMARY OF THE INVENTION

Accordingly, one object of the present invention is to provide deuterium-enriched oseltamivir or a pharmaceutically acceptable salt thereof.

It is another object of the present invention to provide pharmaceutical compositions comprising a pharmaceutically acceptable carrier and a therapeutically effective amount of at least one of the deuterium-enriched compounds of the present invention or a pharmaceutically acceptable salt thereof.

It is another object of the present invention to provide a method for treating a disease selected from prophylaxis, Influenzavirus A, and Influenzavirus B, comprising administering to a host in need of such treatment a therapeutically effective amount of at least one of the deuterium-enriched compounds of the present invention or a pharmaceutically acceptable salt thereof.

It is another object of the present invention to provide a novel deuterium-enriched oseltamivir or a pharmaceutically acceptable salt thereof for use in therapy.

It is another object of the present invention to provide the use of a novel deuterium-enriched oseltamivir or a pharmaceutically acceptable salt thereof for the manufacture of a medicament (e.g., for the treatment of prophylaxis, Influenzavirus A, and Influenzavirus B).

These and other objects, which will become apparent during the following detailed description, have been achieved by the inventor's discovery of the presently claimed deuterium-enriched oseltamivir.

DETAILED DESCRIPTION OF PREFERRED EMBODIMENTS

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts.

All percentages given for the amount of deuterium present are mole percentages.

It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

The present invention provides deuterium-enriched oseltamivir or a pharmaceutically acceptable salt thereof. There are twenty-eight hydrogen atoms in the oseltamivir portion of oseltamivir as show by variables $R_1$-$R_{28}$ in formula I below.

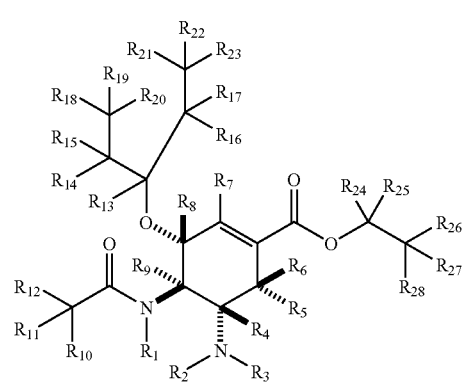

The hydrogens present on oseltamivir have different capacities for exchange with deuterium. Hydrogen atoms $R_1$-$R_3$ are easily exchangeable under physiological conditions and, if replaced by deuterium atoms, it is expected that they will readily exchange for protons after administration to a patient. The remaining hydrogen atoms are not easily exchangeable and may be incorporated by the use of deuterated starting materials or intermediates during the construction of oseltamivir.

The present invention is based on increasing the amount of deuterium present in oseltamivir above its natural abundance. This increasing is called enrichment or deuterium-enrichment. If not specifically noted, the percentage of enrichment refers to the percentage of deuterium present in the compound, mixture of compounds, or composition. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Since there are 28 hydrogens in oseltamivir, replacement of a single hydrogen atom with deuterium would result in a molecule with about 4% deuterium enrichment. In order to achieve enrichment less than about 4%, but above the natural abundance, only partial deuteration of one site is required. Thus, less than about 4% enrichment would still refer to deuterium-enriched oseltamivir.

With the natural abundance of deuterium being 0.015%, one would expect that for approximately every 6,667 molecules of oseltamivir (1/0.00015=6,667), there is one naturally occurring molecule with one deuterium present. Since oseltamivir has 28 positions, one would roughly expect that for approximately every 186,676 molecules of oseltamivir (28×6,667), all 28 different, naturally occurring, mono-deuterated oseltamivirs would be present. This approximation is a rough estimate as it doesn't take into account the different exchange rates of the hydrogen atoms on oseltamivir. For naturally occurring molecules with more than one deuterium, the numbers become vastly larger. In view of this natural abundance, the present invention, in an embodiment, relates to an amount of an deuterium enriched compound, whereby the enrichment recited will be more than naturally occurring deuterated molecules.

In view of the natural abundance of deuterium-enriched oseltamivir, the present invention also relates to isolated or purified deuterium-enriched oseltamivir. The isolated or purified deuterium-enriched oseltamivir is a group of molecules whose deuterium levels are above the naturally occurring levels (e.g., 4%). The isolated or purified deuterium-enriched oseltamivir can be obtained by techniques known to those of skill in the art (e.g., see the syntheses described below).

The present invention also relates to compositions comprising deuterium-enriched oseltamivir. The compositions require the presence of deuterium-enriched oseltamivir which is greater than its natural abundance. For example, the compositions of the present invention can comprise (a) a μg of a deuterium-enriched oseltamivir; (b) a mg of a deuterium-enriched oseltamivir; and, (c) a gram of a deuterium-enriched oseltamivir.

In an embodiment, the present invention provides an amount of a novel deuterium-enriched oseltamivir.

Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a pharmaceutical. Industrial/commercial scale refers to the amount of product that would be produced in a batch that was designed for clinical testing, formulation, sale/distribution to the public, etc.

In another embodiment, the present invention provides a novel, deuterium enriched compound of formula I or a pharmaceutically acceptable salt thereof.

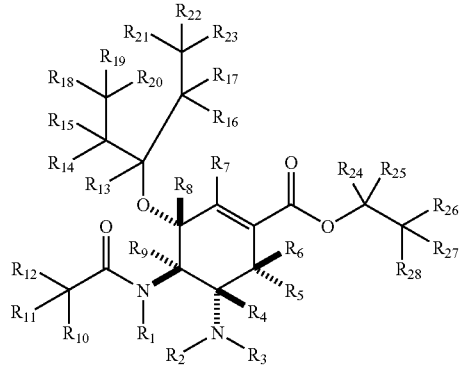

I wherein $R_1$-$R_{28}$ are independently selected from H and D; and the abundance of deuterium in $R_1$-$R_{28}$ is at least 4%. The abundance can also be (a) at least 7%, (b) at least 14%, (c) at least 21%, (d) at least 29%, (e) at least 36%, (f) at least 43%, (g) at least 50%, (h) at least 57%, (i) at least 64%, (j) at least 71%, (k) at least 79%, (l) at least 86%, (m) at least 92%, and (n) 100%.

In another embodiment, the present invention provides a novel, deuterium enriched compound of formula I or a pharmaceutically acceptable salt thereof, wherein the abundance of deuterium in $R_1$-$R_3$ is at least 33%. The abundance can also be (a) at least 67%, and (b) 100%.

In another embodiment, the present invention provides a novel, deuterium enriched compound of formula I or a pharmaceutically acceptable salt thereof, wherein the abundance of deuterium in $R_4$-$R_9$ is at least 17%. The abundance can also be (a) at least 33%, (b) at least 50%, (c) at least 67%, (d) at least 83%, and (e) 100%.

In another embodiment, the present invention provides a novel, deuterium enriched compound of formula I or a pharmaceutically acceptable salt thereof, wherein the abundance of deuterium in $R_{10}$-$R_{12}$ is at least 33%. The abundance can also be (a) at least 67%, and (b) 100%.

In another embodiment, the present invention provides a novel, deuterium enriched compound of formula I, wherein the abundance of deuterium in $R_{13}$-$R_{23}$ is at least 9%. The abundance can also be (a) at least 18%, (b) at least 27%, (c) at least 36%, (d) at least 45%, (e) at least 56%, (f) at least 64%, (g) at least 73%, (h) at least 82%, (i) at least 91%, and (j) 100%.

In another embodiment, the present invention provides a novel, deuterium enriched compound of formula I or a pharmaceutically acceptable salt thereof, wherein the abundance of deuterium in $R_{24}$-$R_{28}$ is at least 20%. The abundance can also be (a) at least 40%, (b) at least 60%, (c) at least 80%, and (d) 100%.

In another embodiment, the present invention provides a novel, isolated deuterium enriched compound of formula I or a pharmaceutically acceptable salt thereof.

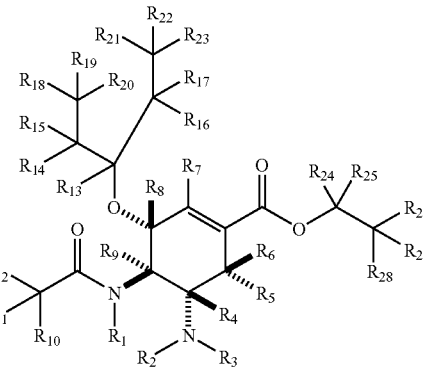

I wherein $R_1$-$R_{28}$ are independently selected from H and D and the abundance of deuterium in $R_1$-$R_{28}$ is at least 4%. The abundance can also be (a) at least 7%, (b) at least 14%, (c) at least 21%, (d) at least 29%, (e) at least 36%, (f) at least 43%, (g) at least 50%, (h) at least 57%, (i) at least 64%, (j) at least 71%, (k) at least 79%, (l) at least 86%, (m) at least 92%, and (n) 100%.

In another embodiment, the present invention provides a novel, isolated deuterium enriched compound of formula I or a pharmaceutically acceptable salt thereof, wherein the abundance of deuterium in $R_1$-$R_3$ is at least 33%. The abundance can also be (a) at least 67%, and (b) 100%.

In another embodiment, the present invention provides a novel, isolated deuterium enriched compound of formula I or a pharmaceutically acceptable salt thereof, wherein the abundance of deuterium in $R_4$-$R_9$ is at least 17%. The abundance can also be (a) at least 33%, (b) at least 50%, (c) at least 67%, (d) at least 83%, and (e) 100%.

In another embodiment, the present invention provides a novel, isolated deuterium enriched compound of formula I or a pharmaceutically acceptable salt thereof, wherein the abundance of deuterium in $R_{10}$-$R_{12}$ is at least 33%. The abundance can also be (a) at least 67%, and (b) 100%.

In another embodiment, the present invention provides a novel, isolated deuterium enriched compound of formula I, wherein the abundance of deuterium in $R_{13}$-$R_{23}$ is at least 9%. The abundance can also be (a) at least 18%, (b) at least 27%, (c) at least 36%, (d) at least 45%, (e) at least 56%, (f) at least 64%, (g) at least 73%, (h) at least 82%, (i) at least 91%, and (j) 100%.

In another embodiment, the present invention provides a novel, isolated deuterium enriched compound of formula I or a pharmaceutically acceptable salt thereof, wherein the abundance of deuterium in $R_{24}$-$R_{28}$ is at least 20%. The abundance can also be (a) at least 40%, (b) at least 60%, (c) at least 80%, and (d) 100%.

In another embodiment, the present invention provides novel mixture of deuterium enriched compounds of formula I or a pharmaceutically acceptable salt thereof.

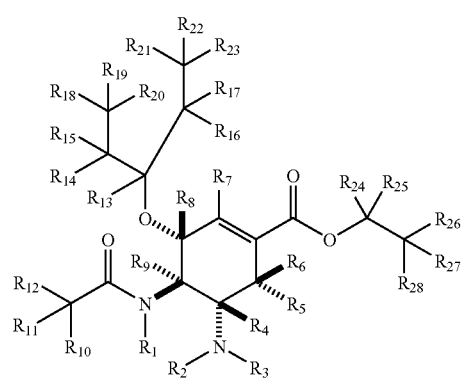

I wherein $R_1$-$R_{28}$ are independently selected from H and D and the abundance of deuterium in $R_1$-$R_{28}$ is at least 4%. The abundance can also be (a) at least 7%, (b) at least 14%, (c) at least 21%, (d) at least 29%, (e) at least 36%, (f) at least 43%, (g) at least 50%, (h) at least 57%, (i) at least 64%, (j) at least 71%, (k) at least 79%, (l) at least 86%, (m) at least 92%, and (n) 100%.

In another embodiment, the present invention provides a novel mixture of deuterium enriched compound of formula I or a pharmaceutically acceptable salt thereof, wherein the abundance of deuterium in $R_1$-$R_3$ is at least 33%. The abundance can also be (a) at least 67%, and (b) 100%.

In another embodiment, the present invention provides a novel mixture of deuterium enriched compound of formula I or a pharmaceutically acceptable salt thereof, wherein the abundance of deuterium in $R_4$-$R_9$ is at least 17%. The abundance can also be (a) at least 33%, (b) at least 50%, (c) at least 67%, (d) at least 83%, and (e) 100%.

In another embodiment, the present invention provides a novel mixture of deuterium enriched compound of formula I or a pharmaceutically acceptable salt thereof, wherein the abundance of deuterium in $R_{10}$-$R_{12}$ is at least 33%. The abundance can also be (a) at least 67%, and (b) 100%.

In another embodiment, the present invention provides a novel mixture of deuterium enriched compound of formula I, wherein the abundance of deuterium in $R_{13}$-$R_{23}$ is at least 9%. The abundance can also be (a) at least 18%, (b) at least 27%, (c) at least 36%, (d) at least 45%, (e) at least 56%, (f) at least 64%, (g) at least 73%, (h) at least 82%, (i) at least 91%, and (j) 100%.

In another embodiment, the present invention provides a novel mixture of deuterium enriched compound of formula I or a pharmaceutically acceptable salt thereof, wherein the abundance of deuterium in $R_{24}$-$R_{28}$ is at least 20%. The abundance can also be (a) at least 40%, (b) at least 60%, (c) at least 80%, and (d) 100%.

In another embodiment, the present invention provides novel pharmaceutical compositions, comprising: a pharmaceutically acceptable carrier and a therapeutically effective amount of a deuterium-enriched compound of the present invention.

In another embodiment, the present invention provides a novel method for treating a disease selected from prophylaxis, Influenzavirus A, and Influenzavirus B comprising: administering to a patient in need thereof a therapeutically effective amount of a deuterium-enriched compound of the present invention.

In another embodiment, the present invention provides an amount of a deuterium-enriched compound of the present invention as described above for use in therapy.

In another embodiment, the present invention provides the use of an amount of a deuterium-enriched compound of the present invention for the manufacture of a medicament (e.g., for the treatment of prophylaxis, Influenzavirus A, and Influenzavirus B).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

The examples provided in the definitions present in this application are non-inclusive unless otherwise stated. They include but are not limited to the recited examples.

The compounds of the present invention may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. All processes used to prepare compounds of the present invention and intermediates made therein are considered to be part of the present invention. All tautomers of shown or described compounds are also considered to be part of the present invention.

"Host" preferably refers to a human. It also includes other mammals including the equine, porcine, bovine, feline, and canine families.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

SYNTHESIS

Scheme 1 shows a route to oseltamivir, which is a combination of two routes. The route from (−)-shikimic acid 1 to the epoxide 9 is from Federspiel, et al., *Org. Proc. Res. Dev.* 1999, 3, 266-274. The remainder of the route from 9 to oseltamivir phosphate is from Rohloff, et al., *J. Org. Chem.* 1998, 63, 4545. See also Bischofberger, et al., U.S. Pat. No. 5,763,483.

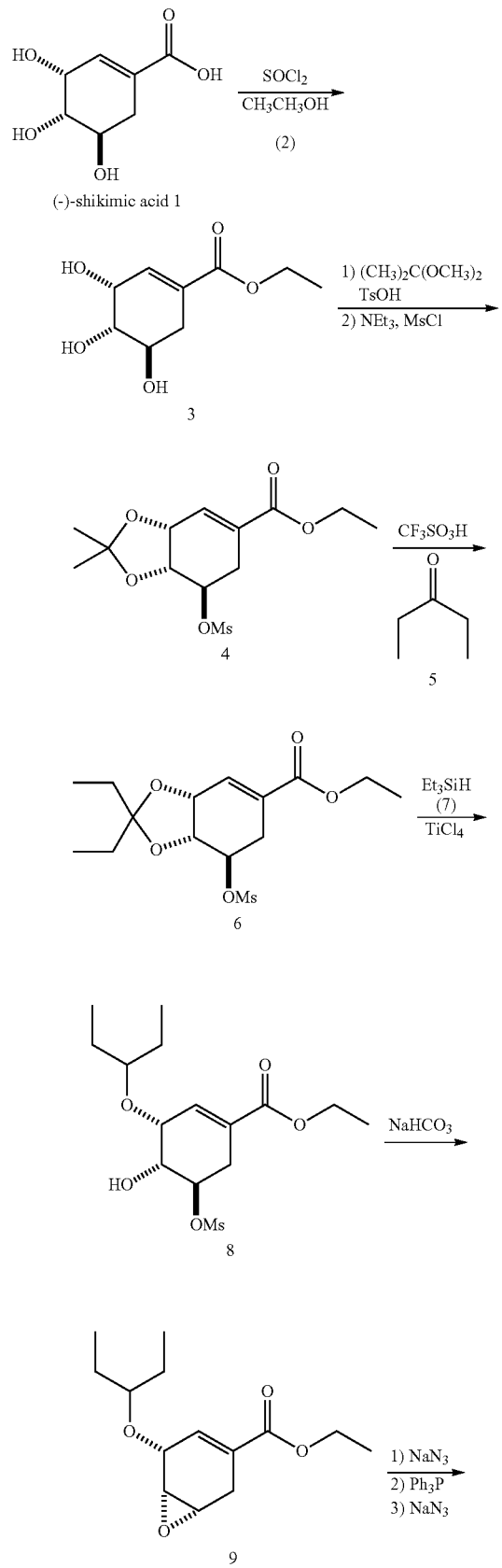

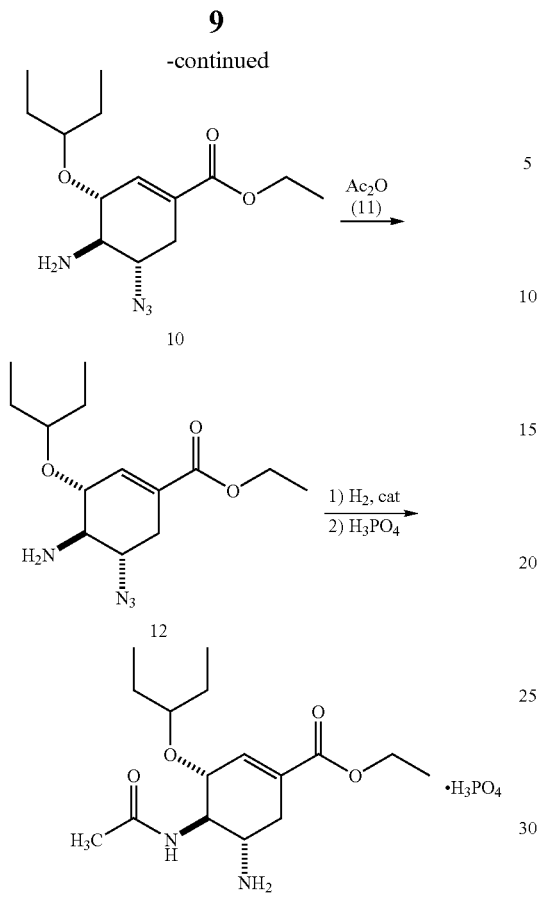

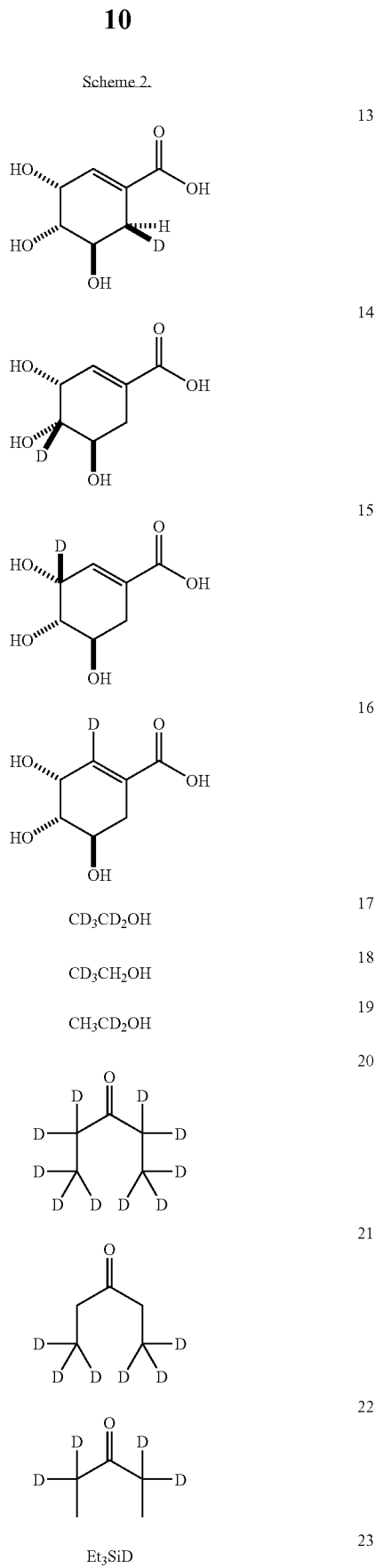

Scheme 2.

Scheme 2 shows how various deuterated starting materials and intermediates can be used in the chemistry of Scheme 1 to make deuterated oseltamivir analogs. A person skilled in the art of organic synthesis will recognize that these materials may be used in various combinations to access many other deuterated oseltamivirs that are not shown. There are several known deuterated forms of (−)-shikimic acid, i.e., 13-16. If 13 is used in place of 1 in Scheme 1, oseltamivir with $R_6$=D results. If 14 is used in place of 1 in Scheme 1, oseltamivir with $R_9$=D results. If 15 is used in place of 1 in Scheme 1, oseltamivir with $R_8$=D results. If 16 is used in place of 1 in Scheme 1, oseltamivir with $R_7$=D results. The use of various commercially available deuterated forms of ethanol, i.e., 17-19, in place of normal ethanol (2) in Scheme 1 results in deuterated oseltamivirs. If 17 is used in place of 2 in Scheme 1, oseltamivir with $R_{24}$-$R_{28}$ results. If 18 is used in place of 2 in Scheme 1, oseltamivir with $R_{26}$-$R_{28}$ results. If 19 is used in place of 2 in Scheme 1, oseltamivir with $R_{24}$-$R_{25}$ results. The use of various commercially available deuterated forms of 3-pentanone, i.e., 20-22, in place of normal 3-pentanone (5) in Scheme 1 results in deuterated oseltamivirs. If 20 is used in place of 5 in Scheme 1, oseltamivir with $R_{14}$-$R_{23}$=D results. To avoid unwanted exchange, $CF_3SO_3D$ should be used as the catalyst in the ketal exchange reaction between 4 and 20. If 21 is used in place of 5 in Scheme 1, oseltamivir with $R_{18}$-$R_{23}$=D results. If 22 is used in place of 5 in Scheme 1, oseltamivir with $R_{14}$-$R_{17}$=D results. To avoid unwanted exchange, $CF_3SO_3D$ should be used as the catalyst in the ketal exchange reaction between 4 and 22. If $Et_3SiD$ (23) is used in place of 7 in Scheme 1, oseltamivir with $R_{13}$=D results. If hexadeuterioacetic anhydride (24) is used in place of 11 in Scheme 1, oseltamivir with $R_{10}$-$R_{12}$=D results.

11
-continued
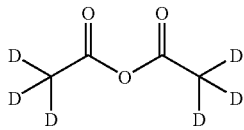
24
EXAMPLES
Table 1 provides compounds that are representative examples of the present invention. When one of $R_1$-$R_{28}$ is present, it is selected from H or D.
1
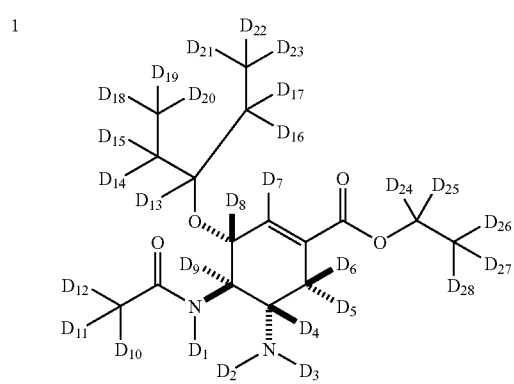
2
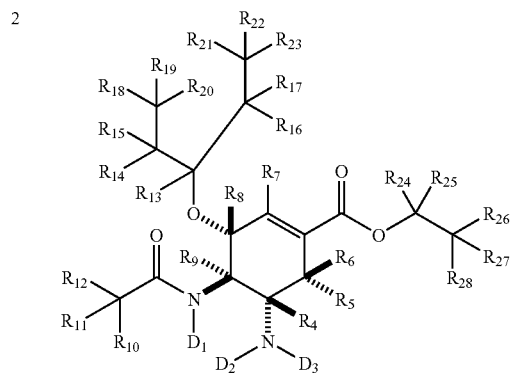
3
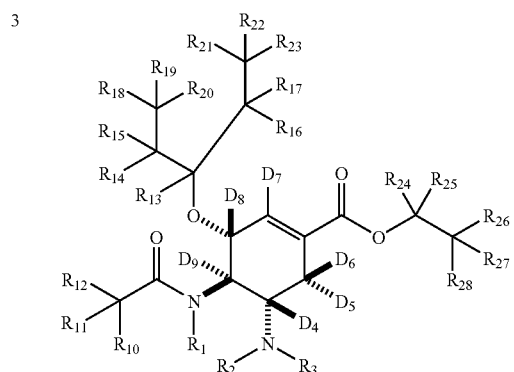
12
-continued
4
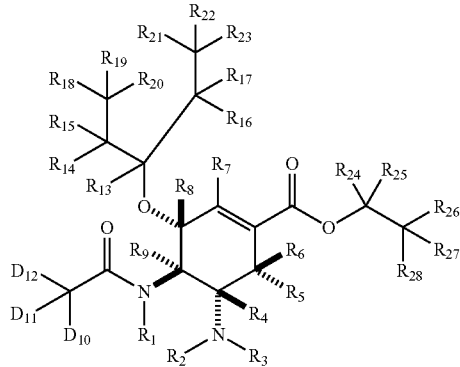
5
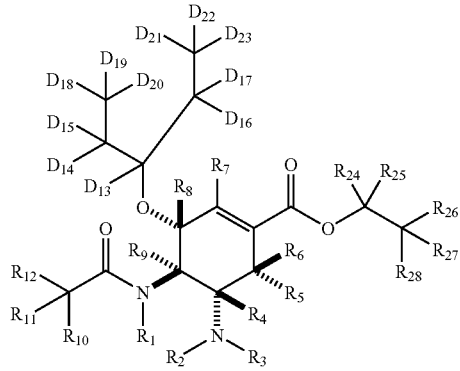
6
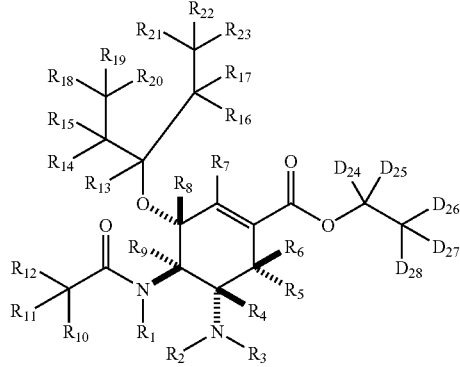
Table 2 provides compounds that are representative examples of the present invention. Where H is shown, it represents naturally abundant hydrogen.

7

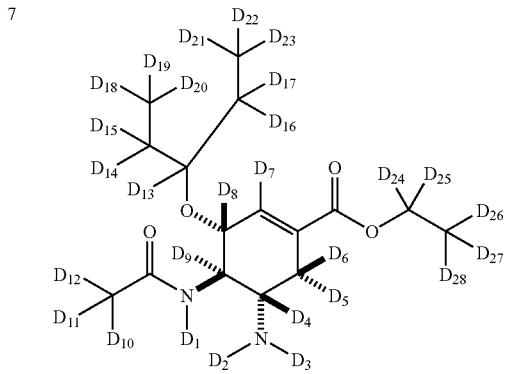

12

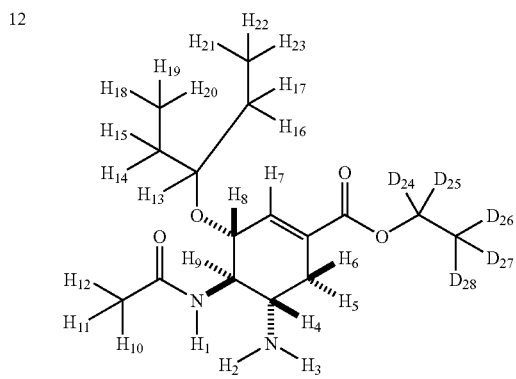

Numerous modifications and variations of the present invention are possible in light of the above teachings. It is therefore to be understood that within the scope of the appended claims, the invention may be practiced otherwise that as specifically described herein.

8

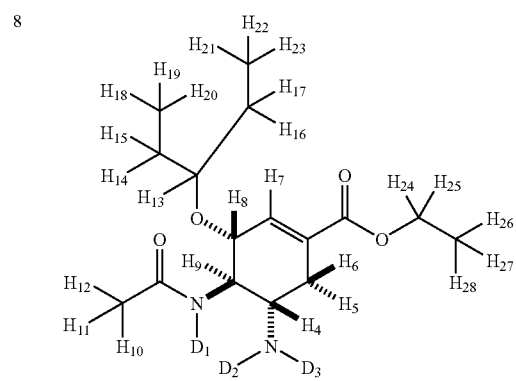

9

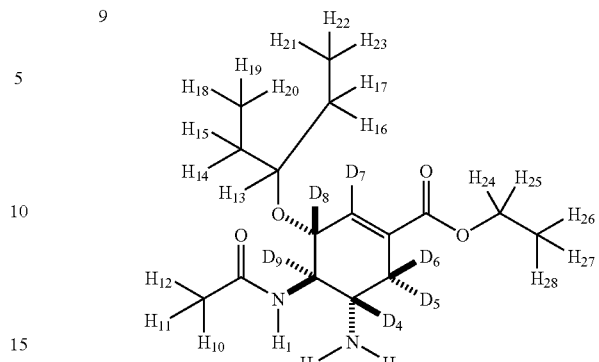

10

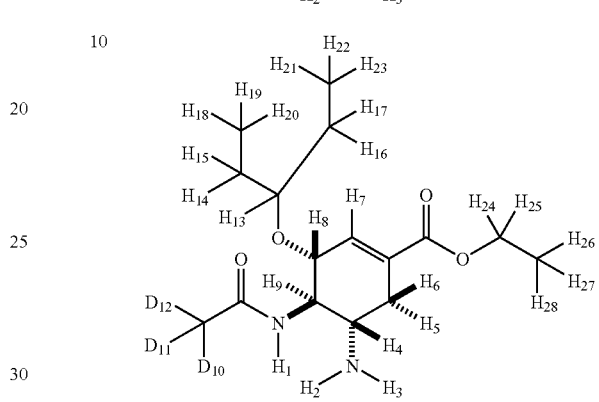

11

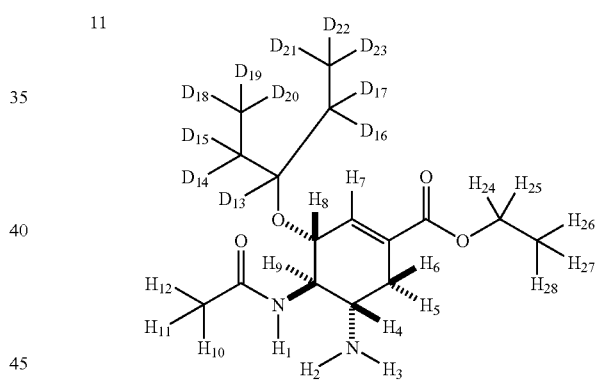

What is claimed is:

1. A deuterium-enriched compound of the formula:

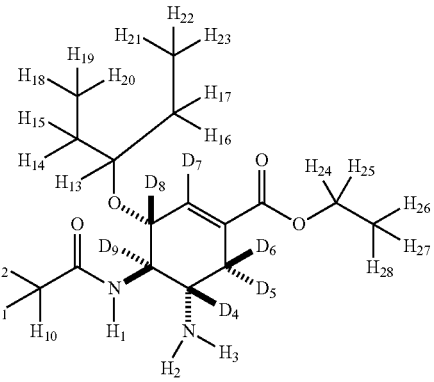

or a pharmaceutically acceptable salt form thereof.

2. A pharmaceutical composition, comprising: a pharmaceutically acceptable carrier and a therapeutically effective amount of the compound of formula:

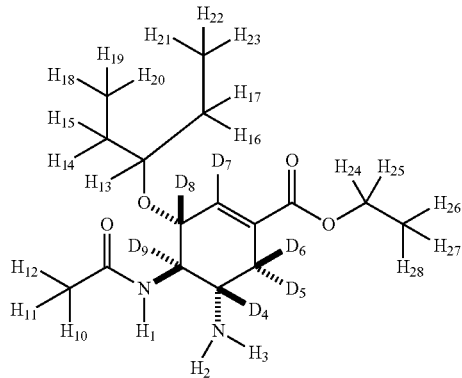

or a pharmaceutically acceptable salt form thereof.

3. A method for treating a disease selected from Influenza virus A and Influenza virus B comprising: administering, to a patient in need thereof, a therapeutically effective amount of the compound of formula:

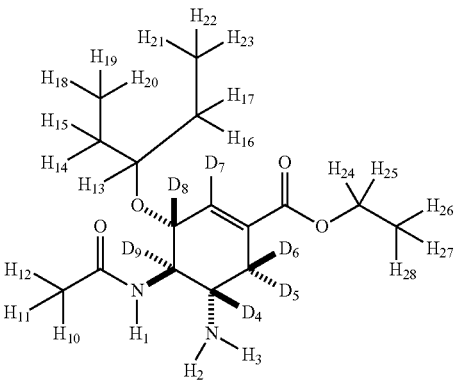

or a pharmaceutically acceptable salt form thereof.

* * * * *